(12) United States Patent
Hassard

(10) Patent No.: US 6,752,914 B1
(45) Date of Patent: Jun. 22, 2004

(54) CAPILLARY ELECTROPHORESIS DEVICE

(75) Inventor: John Hassard, London (GB)

(73) Assignee: Deltadot Limited (GB)

( * ) Notice: Subject to any disclaimer, the term of this patent is extended or adjusted under 35 U.S.C. 154(b) by 0 days.

(21) Appl. No.: 09/623,884
(22) PCT Filed: Mar. 12, 1999
(86) PCT No.: PCT/GB99/00742
§ 371 (c)(1),
(2), (4) Date: Nov. 15, 2000
(87) PCT Pub. No.: WO99/46590
PCT Pub. Date: Sep. 16, 1999

(30) Foreign Application Priority Data

Mar. 12, 1998 (GB) ............................................. 9805301

(51) Int. Cl.[7] ........................ G01N 27/26; G01N 27/447
(52) U.S. Cl. ....................... 204/603; 204/451; 204/452; 204/601
(58) Field of Search ................................. 204/450, 451, 204/452, 600, 601, 603; 356/344

(56) References Cited

U.S. PATENT DOCUMENTS

| 5,571,410 | A | * | 11/1996 | Swedberg et al. | ...... 204/451 X |
| 5,757,482 | A | * | 5/1998 | Fuchs et al. | ................ 356/246 |
| 5,867,266 | A | * | 2/1999 | Craighead | .................... 356/344 |
| 6,011,296 | A | * | 1/2000 | Hassard et al. | ............. 257/448 |
| 6,017,435 | A | * | 1/2000 | Hassard et al. | ............. 204/612 |
| 6,103,533 | A | * | 8/2000 | Hassard et al. | ............... 436/57 |
| 6,236,097 | B1 | * | 5/2001 | Hassard et al. | ............. 257/459 |
| 6,613,210 | B1 | * | 9/2003 | Hassard et al. | ............. 204/461 |

OTHER PUBLICATIONS

Hendry & Hannan, "Detection and Quantitation of Unlabeled Nucleic Acids in Polyacryalmide Gels" Bio Techniques, vol. 20. N 2 (1996) 258–264.*

A. R. Mahon, "Preliminary results from a Novel CVD Diamond Detector System for Molecular Imaging Applications" IEEE Nuclear Science Symposium Conference Record, Anaheim CA, (Nov. 2–9, 1996) 1462–1466.*

A. R. Mahon et al., "Preliminary results from CVD diamond detectors for biomolecular imaging" Nuclear Instruments and Methods in Physics Research A, vol. 392 (1997) 274–280.*

Joseph Wang et al., "Microchip Capillary Electrophoresis Coupled with Boron–Doped Diamond Electrode–Based Electrochemic Detector" Analytical chemistry, vol. 75, No. 4, (2003) 935–939.*

* cited by examiner

Primary Examiner—Nam Nguyen
Assistant Examiner—John S. Starsiak, Jr.
(74) Attorney, Agent, or Firm—Woodard, Emhardt, Moriarty, McNett & Henry LLP

(57) ABSTRACT

An analyser comprises a substrate (20) of diamond, sapphire or a polymer material; an array (10) of elongate capillary channels formed in the substrate; means (40) for driving a sample to be tested along one or more of the channels whereby the velocities of components of the sample along the channels depends on the relative molecular weights of those components; and a radiation source (100) and a radiation detector (30) disposed on either side of the channel array so as to detect the presence of material in the channels as interruptions in the radiation path between the radiation source and the radiation detector.

16 Claims, 3 Drawing Sheets

CAPILLARY ELECTROPHORESIS DEVICE

This application claims the benefit of PCT Application No. PCT/GB99/00742, filed Mar. 12, 1999.

This invention relates to analysers. Embodiments of the invention relate to instruments for the determination of molecular characteristics, such as the length of nucleic acid in terms of base pairs, and the sequencing of genetic samples.

BACKGROUND OF THE INVENTION

There are several current techniques for analysing materials such as DNA samples in an automated or semi-automated manner. One such technique which has been demonstrated for DNA analysis is the use of so-called microfabricated capillary electrophoresis (CE) chips.

These devices comprise a substrate in which a number of very fine capillary chancels are etched and filled with a gel material. A material to be analysed passes along the capillary channel wider the influence of an electric field. Components of the material—for example, nucleic acids—progress along the channel at different rates depending on the relative molecular weights of the components, leading to a separation by molecular weight.

Current techniques use photographic techniques to image radioactive or luminescent tags attached to the nucleic acids. This is a time consuming process. A quicker but expensive alterative is to use phosphor imagers to record the sequences. Furthermore, both processes use hazardous chemicals to tag the nucleic acids and the safe use and disposal of these is a major problem, requiring skilful scientific and technical input.

As mentioned above, all of these techniques are relatively slow. In any current emission technique, such as CE-laser induced fluorescence (CE-UP) the time-to-sequence depends on the separation gradient (i.e. the electric field) and the discriminator power (e.g. the capillary or electrophoresis gel) convolved with the size of the objects to be separated.

There is a need for an improved technique offering a faster response than current techniques and avoiding the use of hazardous materials.

PCT/GB96/01121 discloses an electrophoresis system in which material components are driven along quartz tubes. In effect, the shadow of the separated components is detected by directing an ultraviolet (UV) light from one side of the tubes towards a detector at the other side.

SUMMARY OF THE INVENTION

This invention provides analyser comprising: a substrate of diamond, sapphire or a polymer material; an array of one or more elongate capillary channels formed in the substrate; means for driving a sample to be tested along one or more of the channels whereby the velocities of components of the sample along the channels depends on the relative molecular weights of those components; a radiation source and a radiation detector disposed on either side of the channel array so as to detect the presence of material in the channels as interruptions in the radiation path between the radiation source and the radiation detector.

The invention addresses the above problems by providing a new selection of substrates offering many advantages over the glass, quartz and plastics of previous analysers. In particular, the whole apparatus can be miniaturised and the use of hazardous markers is avoided by detecting the "shadow" of separated components (e.g. DNA fragments).

Embodiments of the invention can provide an analysis technique which can be carried out while avoiding the use of mutagenic, toxic and carcinogenic chemiluminescent, bioluminescent and radiolabels, with associated benefits in running costs, safety and ease of disposal.

Embodiments of the invention can provide up to an order of magnitude increase in speed for DNA sequencing. For example, a sequence of 500 base pairs which might take 6 hours using a conventional electrophoresis technique could be achieved in 10 minutes using a prototype embodiment of the invention. The saving in time can arise because in current imaging techniques the images of bands identified by conventional labels is heavily smeared by the isotropic emission characteristics of the labels, whereas in embodiments of the present invention the image of a nucleic acid band is substantially the same size as the band, smeared only by diffraction.

Embodiments of the invention can further provide an improved detection sensitivity and signal-to-noise ratio in sub-microlitre sequencing and imaging.

Embodiments of the invention can allow pre-programmed sequence recognition masks to accompany an installation, so that in principle a "yes-no" answer could be obtained by relatively untrained end-users. A sequence triage system results which, coupled to the potentially low cost of this technology, could result in the use of apparatus according to embodiments of the invention in doctors' surgeries, schools and even on individual researchers' desks.

BRIEF DESCRIPTION OF THE DRAWING

Embodiments of the invention will now be described, by way of example only, with reference to the accompanying drawings in which.

DESCRIPTION OF PREFERRED EMBODIMENT

Figure 1:
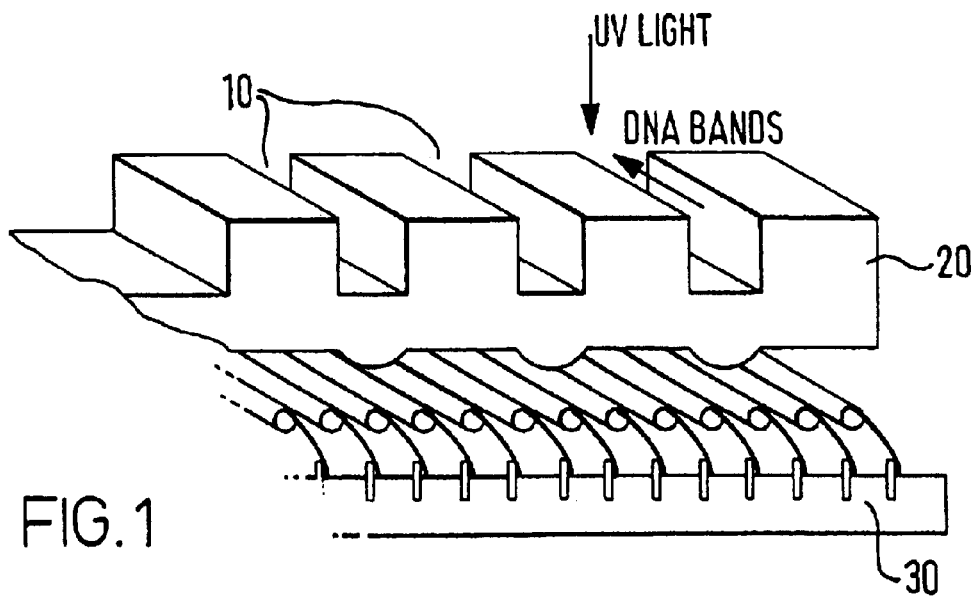
FIG. 1 is a schematic perspective view of part of an analyser according to an embodiment of the invention.

Referring now to FIG. 1, an analyser according to embodiments of the invention comprises an array of channels 10 formed as the substrate is grown or deposited (e.g. by CVD) or etched by excimer laser ablation into a substrate 20 of diamond, sapphire (preferably coated in nanocrystalline diamond) or polymer, possibly deposited on a substrate of a material such as silicon. The channels are at least partially filled by a polyacrylimide gel and are subjected to an electric field along a longitudinal channel direction.

Under the influence of the electric field, DNA samples injected at one end of a channel progress along the channel. Components of the sample progress at a velocity dependent on the molecular weight (often expressed as a number of "base pairs" for DNA samples) of the component.

Ultraviolet light from a light source (not shown in FIG. 1) is directed onto the channels, and transmitted light is imaged by a pixel array 30 of ultraviolet light detectors at the other side of the channels, in effect imaging the shadows of DNA components or bands as they pass along the channels.

At a wavelength of 253.9 nm, a mercury lamp can conveniently be used as the light source.

Each channel is less than 250 $\mu$m deep (preferably about 150 $\mu$m deep), less than 200 $\mu$m wide (preferably 50 $\mu$m wide) and 18 mm long. The DNA samples are driven by the electric field from one end of the channel towards the other, and then the polarity of the electric field is reversed so as to drive the samples in the other direction. This process is repeated many times—e.g. several hundred times and the results averaged.

Results can be obtained by detecting the times at which fragments pass a particular point in the channel, or alternatively by performing a Fourier or other transform on the combined output of the array of spaced pixel detectors to detect velocities along the channel directly (see PCT/GB98/00645). The output of the analyser is thus a velocity map or distribution, whereby lower weight fragments have a higher velocity along the channels than higher weight fragments. Alternatively, an image of the separated components can be generated using an array of pixel detectors, as in PCT/GB96/01121 and analysed directly.

A polymer or diamond lid can be positioned over the channels to avoid contamination.

Figure 2:
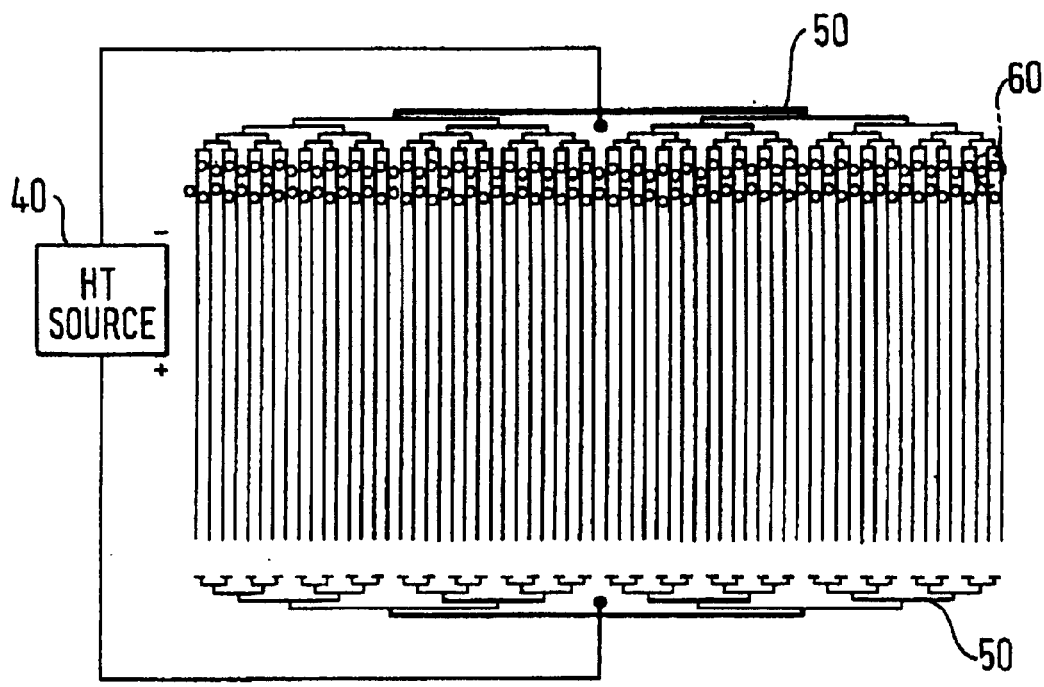
FIG. 2 is a schematic plan view of an array of analyser channels according to an embodiment of the invention.

FIG. 2 is a schematic plan view of an array of channels embodied on a substrate about 20 mm×20 mm in area. A high voltage (HT) source 40 is connected to a tree structure of electrodes 50 at each end of the channels so that an electric field is applied along each channel. Typically the potential difference between ends of the channels may be about 3 kV.

Figure 3:
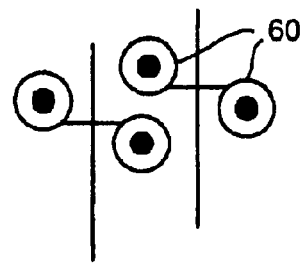
FIG. 3 is an enlarged view of two supply wells.

Supply wells 60 are provided to inject DNA samples into each of the channels. An enlarged view of some supply wells is provided in FIG. 3, showing that they are formed as substantially circular areas of etched material connected to the channels. They can be filled with a robotic micropipette apparatus available from Evotec GmbH.

So, FIG. 2 shows an array of a large number of parallel separation electrophoresis microchannels with associated dendritic branching to and from a buffer well with DNA input and output wells on each channel. DNA may be switched between wells and separation channels using electric fields from suitably positioned electrodes (not shown). In the separation channels it is separated under an electric field as it permeates the electrophoresis gel in the channel—which might be nominally agarose of poly (acrylimide) but other materials are also suitable, such as alcogel or hydrogel so that individual lines corresponding to lengths of DNA become distinct.

Flushing the equipment can be carried out rapidly between input plugs. It is also relatively easy to input a solution to multiple plugs.

Figure 4:
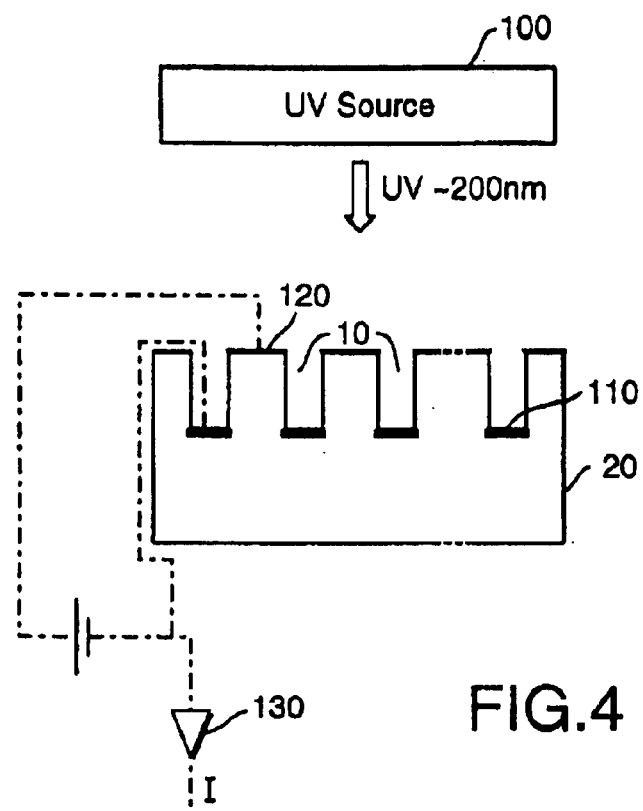
FIG. 4 is a schematic cross sectional view of an analyser operating at a UV wavelength of about 260 nm.
Figure 5:
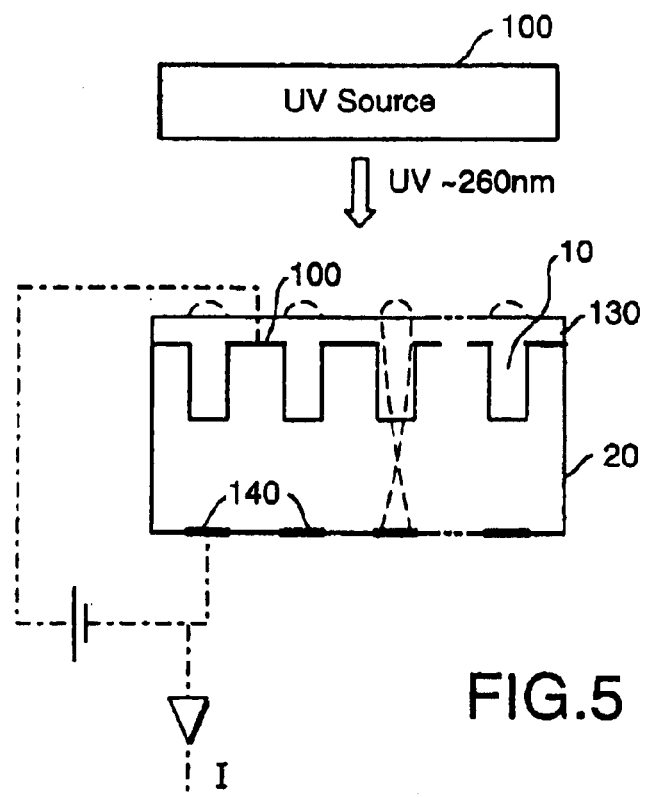
FIG. 5 is a schematic cross sectional view of an analyser channel operating at a UV wavelength of about 200 nm.

FIGS. 4 and 5 schematically illustrate two embodiments of the invention in cross section, one for use at a UV wavelength of about 200 nm (FIG. 4) and one for use at about 260 nm, possibly 253 nm using light from a mercury lamp (FIG. 5).

In each case, channels 10 are etched into a diamond substrate 20. A UV source 100 operating at the relevant wavelength is positioned so as to direct UV light onto the analyser.

In FIG. 4, the lower surface 110 of each channel is made at least partially non-transparent by a treatment such as hydrogenation. When UV light impinges on the surface 110, electron-hole pairs are generated. These can be detected as a photocurrent I by connecting a dc voltage between the surface 110 and a deposited metal layer on a top surface 120 of the substrate. The resulting photocurrent can then be amplified by an amplifier 130.

The signal connections can be made to the surface 110 by depositing an electrically conductive track up the inside of each channel.

The calculation or detection of the concentration of material components between the source and the detector is relatively straightforward, being the difference in detected light levels with and without the band in the way. This is carried out by data processing apparatus such as a general purpose computer (not shown) arranged to receive the output from the detectors.

The source and/or detector can be at a single position with respect to each channel, or can be formed as an array of pixel detectors to image multiple positions on each channel at once.

The advantages of operation at 200 nm arm that the absorption of the light by the DNA fragments is about 10 times higher than that at 253 nm. However, this is weighed against the convenience of operation at 253 nm as a simple source (the mercury lamp) can be used.

FIG. 5 shows a similar arrangement for operation at 253 nm (or, for example, at any wavelength near to 260 nm). Here, a confocal focusing arrangement is used, whereby a microlens fashioned during the etching process onto a diamond lid 130 between each channel and the UV source 100 acts to focus the incident light through the contents of the channels and onto a metallised area 140 at the other face of the diamond substrate. Alternatively, of course, if the positions of the source and detector were swapped, the focusing formations could be formed on what is drawn as the underside of the substrate. Again, electron-hole pairs are created and a photocurrent can be detected by applying a potential difference between a metallised layer 120 and the metalwised area 140.

The systems of FIGS. 4 and 5 can be operated at different wavelengths, and in particular the system of FIG. 4 could be operated at about 200 nm and that of FIG. 5 at about 260 nm.

Diamond as a substrate has a number of particular advantages:

(i) it is chemically inert, hydrophobic and easily cleaned, e.g. using nitric acid;

(ii) it has good thermal conductivity, about 5 times better than copper, so that in embodiments of the invention the entire analyser can be cooled by a Peltier cell at one face of the device;

(iii) it is relatively transparent to UV light, and in particular is one of the most transparent materials known at 257 nm;

(iv) Its surface can be made nontransparent when required, e.g. by hydrogenation;

(v) it has a high breakdown voltage—at least $10^7$ Vcm$^{-1}$;

(vi) it has a very high refractive index, so that surface or other features formed in the diamond can provide at least partial light concentration.

Figure 6:
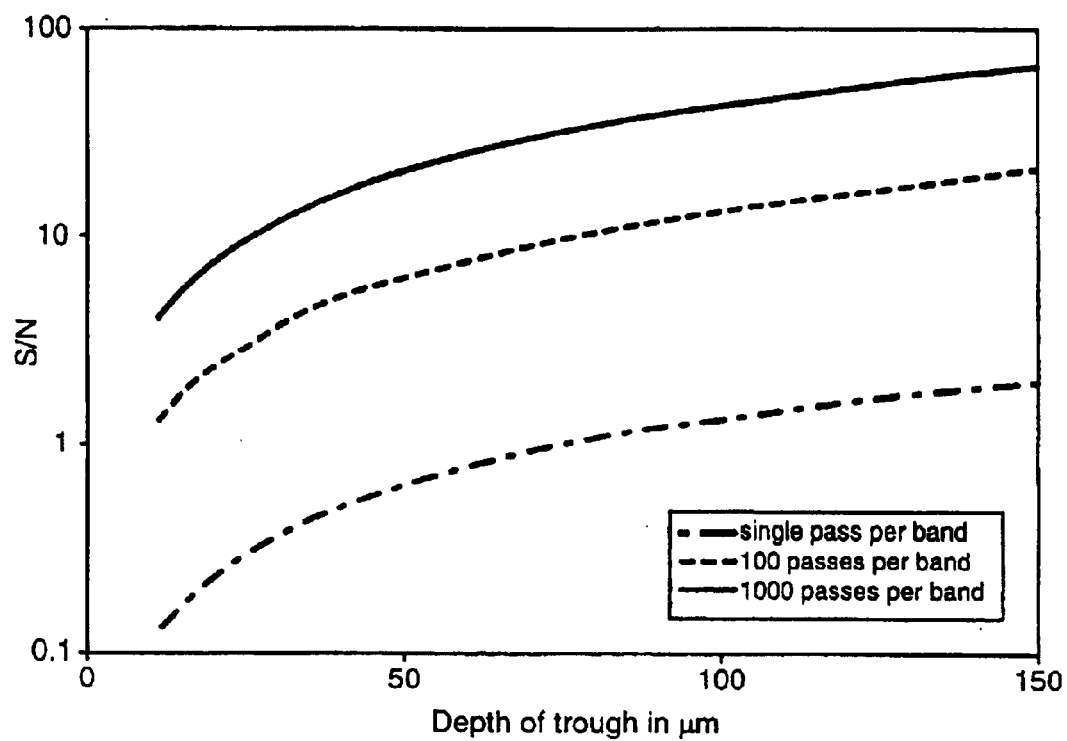
FIG. 6 is a schematic graph illustrating the signal to noise performance of prototype embodiments of the invention.

FIG. 6 is a schematic graph showing the signal to noise (S/N) performance obtainable with embodiments of the invention. A signal to noise ratio of 20:1 is obtained for 2 ng/$\mu$L DNA.

What is claimed is:

1. An analyser comprising:

a substrate of diamond, sapphire or a polymer material;

an array of elongate capillary channels formed in a first surface of the substrate;

means for driving a sample to be tested along the channels whereby the velocities of components of the sample along the channels depend on the relative molecular weights of those components;

a radiation source adjacent the first surface of the substrate and a radiation detector array disposed on either the first surface of the substrate or a second surface of the substrate opposing the first surface of the substrate so as to simultaneously detect the presence of material in the channels as interruptions in the radiation path between the radiation source and the radiation detector array; and wherein the radiation detector array comprises an array of obscured regions on the substrate under the channels, and means for detecting an electric current formed by electron-hole pair generation at the obscured regions.

2. An analyser according to claim 1, in which the substrate is formed of diamond.

3. An analyser according to claim 1, in which the substrate is formed of sapphire having a coating of nanocrystalline diamond.

4. An analyser according to any one of claims 1 to 3, in which the channels are less than 250 um deep.

5. An analyser according to claim 4, in which the channels are less than 150 um deep.

6. An analyser according to claim 1, in which the channels are less than 200 $\mu$m wide.

7. An analyser according to claim 1, in which the channels are less than 100 $\mu$m wide.

8. An analyser according to claim 1, in which the radiation source comprises an ultraviolet light source.

9. An analyser according to claim 8, in which the ultraviolet light source is operable to generate ultraviolet light at a wavelength of about 260 nm or about 200 nm.

10. An analyser according to claim 1, in which the regions are formed on the first surface of the substrate at the bottom of each channel.

11. An analyser according to claim 1, in which the regions are formed on the second surface of the substrate substantially beneath each channel.

12. An analyser comprising:

a substrate of diamond or sapphire material;

an array of elongate capillary channels formed in a first surface of the substrate;

means for driving a sample to be tested along the channels whereby the velocities of components of the sample along the channels depend on the relative molecular weights of those components;

a radiation source adjacent the first surface of the substrate and a radiation detector array disposed on either the first surface of the substrate or a second surface of the substrate opposing the first surface of the substrate so as to simultaneously detect the presence of material in the channels as interruptions in the radiation path between the radiation source and the radiation detector array.

13. An analyser according to claim 12, wherein the substrate is formed of diamond.

14. An analyser according to claim 12, wherein the substrate is formed of sapphire having a coating of nanocrystalline diamond.

15. An analyser according to claim 12, wherein the radiation source comprises an ultraviolet light source operable to generate ultraviolet light at a wavelength of about 260 nm or about 200 nm.

16. An analyser according to claim 12, wherein the radiation detector comprises an array of obscured regions on the substrate under the channels, and means for detecting an electric current formed by electron-hole pair generation at the obscured regions.

\* \* \* \* \*